United States Patent [19]
Johnston

[11] 3,940,392
[45] Feb. 24, 1976

[54] CERTAIN PYRAZINYLOXYPHENYL UREA COMPOUND
[75] Inventor: Howard Johnston, Walnut Creek, Calif.
[73] Assignee: The Dow Chemical Company, Midland, Mich.
[22] Filed: Jan. 22, 1974
[21] Appl. No.: 435,616

[52] U.S. Cl.............................. 260/250 BN; 71/92
[51] Int. Cl.² ..................................... C07D 241/18
[58] Field of Search............................. 260/250 BN

[56] References Cited
UNITED STATES PATENTS
2,666,055   1/1954   Conroy........................ 260/250 BN FOREIGN PATENTS OR APPLICATIONS
6,505,224   10/1965   Netherlands..................... 260/250 R
974,406   11/1964   United Kingdom............. 260/250 R Primary Examiner—Richard J. Gallagher
Attorney, Agent, or Firm—S. Preston Jones; Gary D. Street

[57] ABSTRACT

Disclosed are novel substituted pyrazinyloxy(thio)phenyl urea compounds and derivatives which are useful as herbicides and can be formulated to provide herbicidal compositions.

1 Claim, No Drawings

CERTAIN PYRAZINYLOXYPHENYL UREA COMPOUND

SUMMARY OF THE INVENTION

The present invention is directed to substituted pyrazinyloxy(thio)phenyl urea compounds corresponding to the formula:

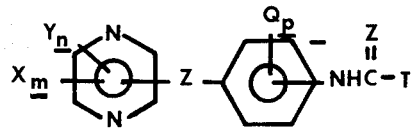

wherein:

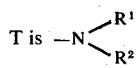

T is $-N\begin{smallmatrix}R^1\\R^2\end{smallmatrix}$ or

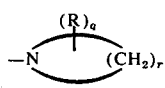

$r$ represents an integer of 4 or 5;
$q$ represents an integer of 0 to 2, inclusive;
each $p$ independently represents an integer of 0 or 1;
each X independently represents bromo, chloro, iodo or fluoro;
$m$ represents an integer of 0 to 2, inclusive;
each Y independently represents cyano, nitro, $ZR^3$, $-C(X')_3$ or

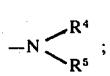

$-N\begin{smallmatrix}R^4\\R^5\end{smallmatrix}$;

$n$ represents an integer of 0 to 2, inclusive, the sum of $m + n$ being from 0 to 2, inclusive;
each X' independently represents hydrogen or halo;
each Z independently represents oxygen or sulfur;
Q represents methyl, ethyl, halo, nitro, cyano or trifluoromethyl;
each R independently represents hydrogen or an alkyl group of from about 1 to about 3 carbon atoms;
$R^1$ represents hydrogen, an alkyl group of from about 1 to about 4 carbon atoms or an alkoxy group of from about 1 to about 4 carbon atoms;
$R^2$ represents an alkyl group of from about 1 to about 3 carbon atoms or

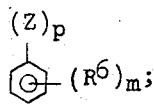

$R^3$ represents an alkyl group of from about 1 to about 3 carbon atoms;
$R^4$ and $R^5$ each independently represent hydrogen or an alkyl group of from about 1 to about 4 carbon atoms; and
each $R^6$ represents halo or an alkyl group of from about 1 to about 3 carbon atoms.

For the sake of brevity and simplicity, the term "active ingredient" is used hereinafter in this specification to broadly describe the compounds of the present invention. In the reaction sequences set forth below, all substituents, unless otherwise expressly indicated, are the same as set forth above.

The active ingredients of the present invention are normally crystalline solids and are soluble in the usual organic solvents, as well as having some solubility in water. The active ingredients are useful as plant growth regulants, and especially as herbicides when applied either as a pre-emergence or post-emergence treatment and may be formulated with the usual herbicide carriers for use in controlling unwanted plants.

DETAILED DESCRIPTION

The active ingredients of the present invention are useful as herbicides and certain of the active ingredients of the present invention have been found suitable for controlling unwanted plants among crops such as, for example rice and wheat, without injury thereto. As used in the present specification and claims, the term "herbicide" means an active ingredient which, when used in a growth controlling amount, controls or modifies the growth of plants. By a "growth controlling amount" is means an amount of compound which causes a modifying effect upon the growth of plants. Such modifying effects include all deviations from natural development, for example, killing, retardation, defoliation, desiccation, regulation, stunting, tillering, and the like. By "plants" it is meant germinant seeds, emerging seedlings, and established vegetation, including the roots and above-ground portions.

The term "alkyl" is used herein and in the appended claims to designate a straight or branched chain alkyl radical containing from 1 to about 4 carbon atoms, such as, for example, methyl, ethyl, propyl, isopropyl, butyl, isobutyl and tert-butyl. The term "alkoxy" as employed designates a straight or a branched-chain radical containing from 1 to about 4 carbon atoms, such as, for example, methoxy, ethoxy, propoxy, isopropoxy, butoxy, isobutoxy and tert-butoxy.

The terms "halo" and "halogen" are employed herein to represent chlorine, fluorine and bromine.

Preferred compounds of the present invention are those compounds wherein $n$ is 0 and $m$ is at least 1. In a further preferred embodiment, $m$ is 0 and $n$ is at least 1. In another embodiment, those compounds wherein the sum of $m + n$ is at least two are preferred. Another class of preferred compounds includes those wherein T is $-NR^1R^2$. A further class of preferred compounds includes those wherein T is $-NR^1R^2$ and $R^1$ and $R^2$ each represent alkyl. Still another preferred class of compounds includes those wherein T is $-NR^1R^2$, $R^1$ is alkoxy and $R^2$ is alkyl. In still another preferred embodiment, T is

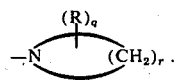

The active ingredients of the present invention wherein T is $-NR^1R^2$ and wherein $R^1$ and $R^2$ are hydrogen or alkyl, conveniently hereinafter referred to as "pyrazinylurea" compounds, are readily prepared by reacting a selected substituted pyrazinylbenzenamine reactant with a selected substituted carbamoyl halide reactant. The pyrazinylbenzenamine reactant is prepared by reacting a corresponding pyrazinylnitrobenzene reactant, which is obtained by reacting a selected substituted nitro(thio)phenol reactant with a selected substituted halopyrazine reactant, with a reducing agent. Such reaction sequence is illustrated as follows:

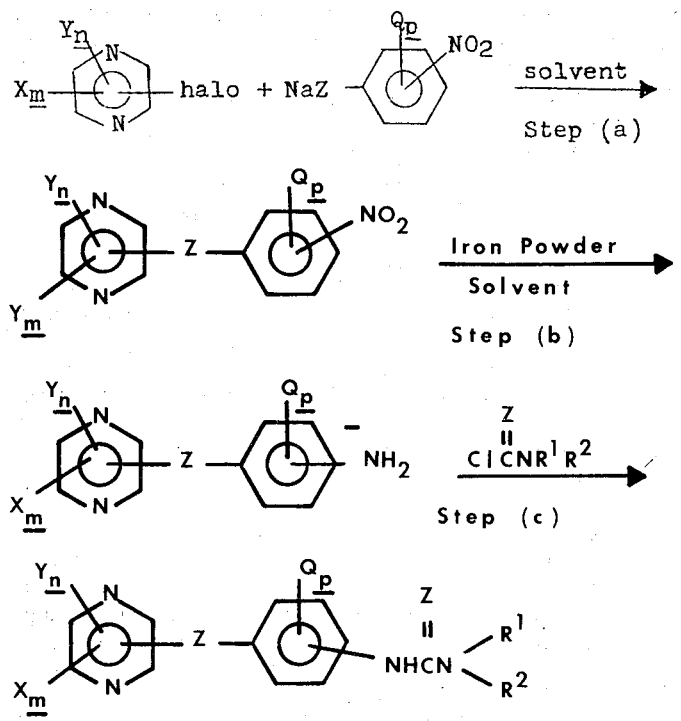

Reaction I

The reaction in Step (a) above proceeds readily under ambient atmospheric pressure at reaction temperatures of from about 100° to about 160°C. for a period of from about 3 to about 5 hours. In such operations, the salt of the substituted nitrophenol or nitrothiophenol is mixed with the selected halopyrazine reactant in the presence of an inert solvent, such as, for example, dimethylsulfoxide, and the resulting reaction mixture heated at a temperature within the above indicated ranges. Following the substantial completion of the reaction, the reaction mixture is cooled and mixed with cold water. The resulting product precipitate is recovered by filtration and recrystallized according to conventional techniques from a solvent such as acetonitrile, methylenechloride, or the like.

The substituted nitrophenate solution is prepared by rapidly adding stoichiometric proportions of the substituted nitro(thio)phenol reactant to a solution of sodium metal in methanol. The sodium nitro(thio)phenate solution is usually mixed with the halopyrazine reactant in a solvent carrier, such as previously mentioned. The resulting reaction mixture is maintained at temperatures between about 50° and 100°C., preferably between about 60° and 90°C., for a period of from about 1 to about 3 hours. Following the substantial completion of the reaction, the reaction mixture is cooled to about 50°C., mixed with ice water and the resulting precipitate recovered by filtration, washed with water and dried. The reaction product thus obtained can be employed as is or further purified by recrystallization from a solvent or solvent mixture such as previously mentioned.

The product thus obtained from step (a) of Reaction I is mixed, in the presence of an aqueous alcohol solution, with a reducing agent, such as, for example, iron powder. The resulting reaction mixture is heated to the reflux temperature thereof with vigorous stirring and an alcohol solution of concentrated hydrochloric acid is added thereto, portionwise, over a 10 to 30 minute period. The reaction mixture is heated at the reflux temperature for a period of from about 2 to about 4 hours and filtered while hot. The solid product thus obtained is washed with an aqueous alkanol solution, such as 50–95% ethanol, and the filtrate portions combined and extracted with a solvent such as benzene, methylene chloride or the like. The extract is then dried, treated with activated charcoal, such as Norite, filtered and evaporated to dryness to obtain the desired pyrazinylbenzenamine reactant.

The pyrazinylbenzenamine reactant obtained from step (b) above is reacted with an appropriately substituted carbamoyl halide reactant in the presence of dry pyridine to obtain the desired pyrazinyl urea compounds of the instant invention. The reaction proceeds readily under ambient temperature and pressure conditions. Generally, stoichiometric amounts of the reactants are employed. In carrying out the reaction, the total quantity of the carbamoyl halide reactant is usually added all at once to a solution of the amine reactant in pyridine and the resulting reaction mixture allowed to stand at ambient temperatures for a period of from about 15 to about 30 hours. The reaction mixture is then poured into cold water and allowed to stand for a short period of time. The resulting product precipitate is recovered by filtration and mixed with a solvent, such as one of those hereinbefore mentioned. The resulting solvent-product solution is dried, treated with Norite and concentrated by evaporation to crystallize out the desired pyrazinylurea product.

The pyrrolidine- and piperidine- derivatives of the present invention, i.e., wherein T is

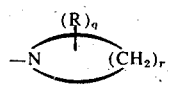

are prepared by reacting the amine intermediates of the present invention (prepared in step (b) of Reaction I) with phosgene or thiophosgene in the presence of toluene to form a corresponding novel pyrazinyloxy(thio)-phenyl iso- or isothio- cyanate intermediate, hereinafter referred to as "isocyanate" intermediates, which can then be reacted with a selected pyrrolidine or piperidine reactant to obtain the desired product. The essential steps of the reaction sequence can be schematically illustrated as follows:

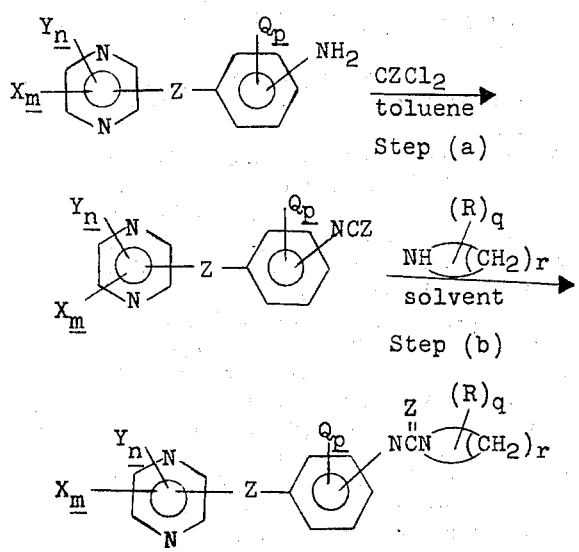

Reaction II

The isocyanate intermediates are readily prepared according to step (a) above by first preparing a solution of phosgene or thiophosgene in a solvent such as, for example, water, toluene or the like, and then rapidly adding, with stirring, a solution of the benzenamine starting material in toluene. The benzenamine addition is regulated so as to maintain the temperature of the mixture at about 5°C. or less, with additional quantities of solvent being added if necessary. Following the completion of the benzenamine addition, the reaction mixture is agitated and heated gradually until a temperature of from about 70 to about 100°C. is reached. The solvent carrier is then removed from the reaction mixture by evaporation under reduced pressure and the remaining residue taken up in hexane which is then cooled to crystallize the desired product. An excess of phosgene or thiophosgene, in a ratio of from about 3 to about 4 moles thereof per mole of benzenamine reactant, is preferably employed in the reaction. During the reaction, excess phosgene can be removed by purging the reaction mixture with an inert gas, such as nitrogen.

In step (b) of Reaction II, the isocyanate intermediate is reacted with the selected pyrrolidine or piperidine reactant under reaction conditions generally the same as for the hereinbefore described procedures in step (c) of Reaction I. Stoichiometric quantities of the reactants are usually employed.

The isocyanate intermediates prepared in step (a) of Reaction IV are also employed in the preparation of compounds of the instant invention wherein T is

and $R^1$ is alkoxy and $R^2$ is alkyl. other pyrazinylurea compounds of the present invention can also be prepared from the isocyanate intermediates. In such operations, the isocyanate intermediates are reacted with an appropriately substituted hydroxyl amine salt reactant in the presence of an inert solvent, such as, for example, pyridine according to the following illustrative reaction sequence:

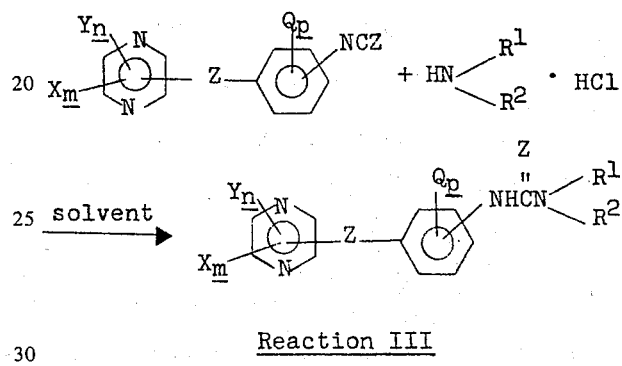

Reaction III

The reaction is conducted under ambient atmospheric pressure at temperatures of from about 50° to about 100°C. Preferably, an actuating agent is employed to increase the reaction rate. Representative actuating agents that can be employed include, for example, tertiary amines such as triethylamine and the like. The reactants are usually employed in stoichiometric proportions while an excess of the actuating agent is employed.

In carrying out the reaction, the isocyanate and substituted hydroxylamine reactants are contacted in the presence of a dry inert solvent containing the actuating agent. Representative solvents include, for example, pyridine, toluene or the like. The resulting reaction mixture is heated with stirring at a temperature within the above described range for a period of from about ½ to about 2 or more hours. The reaction mixture is then stirred at ambient temperatures for a period of from about 1 to about 12 hours and then cooled and mixed with cold water. The resulting product precipitate is recovered and purified in typical procedures previously set forth.

The following example illustrates the present invention and the manner by which it can be practiced but, as such, should not be construed as limitations upon the overall scope of the same.

EXAMPLE 1

N'-(4-((6-chloro-2-pyrazinyl)oxy)benzenamine (6.3 grams; 0.0285 mole) was mixed with dimethylcarbamoyl chloride (3.06 grams, 0.0285 mole) in the presence of about 15 milliliters (ml) of pyridine and the resulting reaction mixture was maintained at ambient temperatures for a period of about 24 hours. Following the substantial completion of the reaction, the reaction mixture was poured into cold water, allowed to stand. The light red product precipitate which formed after about 10 minutes was recovered by filtration, dried, and taken up in hot benzene. The resulting solution was treated with activated charcoal, filtered, and hexane added to the filtrate. A white crystalline solid was obtained upon cooling of the filtrate. As a result of these operations, the desired N'-(4-((6-chloro-2-pyrazinyl)oxy)phenyl)-N,N-dimethylurea product was recovered as a white crystalline solid having a melting point of 158°–160°C.

Other urea compounds and derivatives are similarly prepared from selected substituted amine or isocyanate intermediates in accordance with the procedures of the foregoing Example and the foregoing teachings of the specification. Such other compounds include, inter alia, the following:

N'-(4-((5,6-dichloro-2-pyrazinyl)oxy)phenyl)-N,N-dimethylurea;
N'-(4-((6-methoxy-2-pyrazinyl)oxy)phenyl)-N,N-dimethylurea;
N-butyl-N'-(4-((6-fluoro-2-pyrazinyl)oxy)phenyl)-N-methylurea;
N'-(4-((6-bromo-2-pyrazinyl)oxy)phenyl)-N-methyl-N-methoxyurea;
N-butoxy-N'-(4-((6-iodo-2-pyrazinyl)thio)-3-chlorophenyl)-N-methylurea;
N-butoxy-N-propyl-N'-(4-((5,6-dibromo-2-pyrazinyl)oxy)-3-methylphenyl)urea;
N-(4-((5,6-dichloro-2-pyrazinyl(thio)-3-cyanophenyl)-1-pyrrolidinecarboxamide;
N-(4-((6-(trifluoromethyl)-2-pyrazinyl)thio)-3-nitrophenyl)-1-piperidinecarboxamide;
N-(4-((5-chloro-6-(trifluoromethyl)-2-pyrazinyl)oxy)-3-(trifluoromethyl)phenyl)- 2,5-dimethyl-1-pyrrolidinecarboxamide;
N-((4-chlorophenyl)thio)-N'-(4-((6-chloro-2-pyrazinyl)oxy)phenyl)-N-methylurea;
N'-((4-(6-cyano-2-pyrazinyl)thio)phenyl)-N,N-dimethylurea;
N'-(4-((3,5-bis(trifluoromethyl)-2-pyrazinyl) oxy)phenyl)-N,N-dimethylthiourea;
N'-(3-((5-chloro-2-pyrazinyl)thio)phenyl)-N,N-dimethylthiourea;
N,N-dimethyl-N'-(4-(2-pyrazinyloxy)phenyl)urea;
N,N-dimethyl-N'-(4-((6-nitro-2-pyrazinyl(oxy)phenyl)urea;
N,N-dimethyl-N'-(4-((6-(methylthio)-2-pyrazinyl)oxy)phenyl)urea;
N,N-dimethyl-N'-(4-((6-methyl-2-pyrazinyl)oxy)phenyl)urea;
N'-(4-((6-chloro-3-cyano-2-pyrazinyl)thio)phenyl)-N,N-dimethylurea;
N'-(4-((3-chloro-5,6-dicyano-2-pyrazinyl)oxy)phenyl)-N,N-dimethylurea;
N'-(4-((3-chloro-5-(trifluoromethyl)-2-pyrazinyl)oxy)phenyl)-N-methoxy-N-methylurea;
N-methoxy-N-methyl-N'-(4-((6-(trifluoromethyl)-2-pyrazinyl)oxy)phenyl)thiourea;
N,N-dimethyl-N'-(4-((6-(propylthio)-2-pyrazinyl)oxy)phenyl)urea;
N'-(4-((6-chloro-2-pyrazinyl)oxy)-3-(trifluoromethyl)phenyl)-N,N-dimethylurea;
N,N-dimethyl-N'-(4-((6-isopropoxy)-2-pyrazinyl)oxy)phenyl)urea;
N -(4-((6-chloro-2-pyrazinyl)oxy)phenyl)-2,5-dimethyl-1-pyrrolidinecarboxamide;
N,N-dimethyl-N'-(4-(6-methyl-2-pyrazinyl)oxy)phenyl)thiourea;
N'-(4-((3-chloro-5-(chlorodifluoromethyl)-2-pyrazinyl)oxy)phenyl)-N,N-dimethylurea;
N'-(3-((3,5-dicyano-2-pyrazinyl)oxy-4-ethylphenyl)-N-methoxy-N-methylurea;
N'-(4-((6-(trifluoromethyl)-2-pyrazinyl)thio)-3-cyanophenyl)-N,N-ethylurea;
N-Butyl-N'-(5-((3-chloro-6-methylamino-2-pyrazinyl)thio)-3-bromophenyl)-N-methylthiourea;
N-butoxy-N'-(3-((5-(dichloromethyl)-2-pyrazinyl)oxy)-4-cyanophenyl)-N-propylurea;
N'-(4-((6-methyl-3,5-dichloro-2-pyrazinyl)thio)-3-methylphenyl)-N,N-dimethylurea;
N'-(4-((3,5-dimethyl-6-chloro-2-pyrazinyl)oxy)-3-fluorophenyl)-N-methyl-N-methoxythiourea;
N-(4-((3,6-dinitro-2-pyrazinyl)oxy)phenyl)-3-propyl-1-piperidinecarboxamide;
N-(4-((6-chloro-3,5-dimethoxy-2-pyrazinyl)oxy)-3-chlorophenyl)-2,6-dimethyl-1-piperidinethiocarboxamide;
N'-(5-((6-bromo-5-n-butylamino-2-pyrazinyl)thio)-3-(trifluoromethyl)phenyl)-N-ethoxy-N-methylthiourea;
N'-(3-((5-di-n-butylamino-3-methyl-2-pyrazinyl)oxy)-phenyl)-N,N-dimethylurea;
N-(4-((3,6-dichloro-5-cyano-2-pyrazinyl)thio)-2-chlorophenyl)-1-pyrrolidinecarboxamide;
N'-(4-((3,5-diamino-6-chloro-2-pyrazinyl)oxy)-phenyl)-N,N-dimethylurea;
N'-(5-((6-chloro-3,5-dinitro-2-pyrazinyl)thio)-3-methylphenyl)-N,N-di-n-propylurea;
N-((3,5-di-i-propylphenyl)oxy)-N'-(4-((3,5-bis(trifluoromethyl)-2-pyrazinyl)oxy)-N-methylthiourea;
N'-(4-((3,6-dichloro-5-(difluoromethyl)-2-pyrazinyl)oxy)phenyl)-N,N-dimethylurea;
N'-(4-((3,6-di-(dimethylamino)-2-pyrazinyl)thio)-phenyl)-N-methoxy-N-methylthiourea;
N'-(4-((5-cyano-6-(trifluoromethyl)-2-pyrazinyl)thio)phenyl)-N,N-dimethylthiourea;
N-(4-((3-methyl-6-(trifluoromethyl)-2-pyrazinyl)thio)phenyl-1-piperidinecarboxamide;
N-(4-((5-methyl-6-nitro-2-pyrazinyl)oxy)-3-chlorophenyl)-1-pyrrolidinecarboxamide;
N'-(4-((5-cyano-3-nitro-2-pyrazinyl)thio)phenyl-N-methoxy-N-methylurea;
N'-(4-((3-cyano-6-methylamino-2-pyrazinyl)thio)-phenyl)-N,N-dimethylthiourea;
N'-(4-((3-nitro-5-(trifluoromethyl)-2-pyrazinyl)oxy)-phenyl)-N-methoxy-N-methylurea;
N'-(4-((6-amino-3-(trifluoromethyl)-2-pyrazinyl)thio)-3-methylphenyl)-N,N-dimethylthiourea; and
N'-(3-((6-propylthio-5-(trifluoromethyl)-2-pyrazinyl)oxy)phenyl)-N,N-dimethylurea.

The amine and isocyanate intermediates are readily apparent in view of the foregoing enumerated compounds. Such amine intermediates employed in alternative methods of preparing the pyrazinylurea compounds are of the formula represented in Reaction Sequences I and II of the specification and are prepared in accordance with the teachings of the specification. The nomenclature for such amine intermediates is analogous to the benzenamine reactant named in Example 1. The isocyanate intermediates employed to prepare the pyrimidinyl carboxamide compounds as well as other of the above-enumerated compounds are likewise readily apparent in view of the foregoing compounds. Such isocyanate intermediates correspond to the general formula represented in reaction sequence III set forth hereinbefore and are prepared according to the teachings set forth in the specification. The isocyanate compound employed for the preparation of the compound of Example 1, or other urea or carboxamide compounds, would be N'-(4-((6-chloro-2-pyrazinyl)oxy)phenyl)isocyanate. Other amine and isocyanate intermediates are similarly prepared and named.

The compounds of the present invention have been found to be suitable for use in methods for the pre- and post-emergent control of weeds or other unwanted vegetation. Certain of the active ingredients of the present invention have been found to be active against undesired vegetation in the presence of desired crop plants while producing only a negligible effect on the crop plants. For all such uses, unmodified active ingredients of the present invention can be employed. However, the present invention embraces the use of a herbicidally-effective amount of the active ingredients in composition form with a material known in the art as an adjuvant or carrier in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents used as extending agents there can be employed hydrocarbons, e.g. benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, keiselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)sorbitan monostearate (Tween 60), and sodium dihexyl sulfosuccinate.

The concentration of the active ingredients in liquid compositions generally is from about 0.5 to about 95 percent by weight or more. Concentrations of from about 0.5 to about 50 weight percent are often employed. In dusts or dry formulations, the concentration of the active ingredient can be from about 0.5 to about 95 weight percent or more; concentrations of from about 0.5 to about 50 weight percent are often conveniently employed. In compositions to be employed as concentrates, the active ingredient can be present in a concentration of from about 5 to about 98 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power-dusters, boom and hand sprayers, spray-dusters, by addition to irrigation water, and by other conventional means. The compositions can also be applied from airplanes as a dust or a spray because they are effective in very low dosages.

The exact dosage to be applied is dependent not only upon the specific active ingredient being employed, but also upon the particular plant species to be modified and the stage of growth thereof, as well as the part of the plant to contacted with the toxic active ingredient. Thus, it is to be understood that all of the active ingredients of the invention and compositions containing the same may not be equally effective at similar concentrations or against the same plant species. In non-selective preemergence and foliage treatments the compositions of this invention are usually applied at an approximate rate of from about 1 to about 25 lbs. per acre, but lower or higher rates may be appropriate in some cases. In selective post-emergence operations to foliage, rates of from about 1.25 to about 5.0 pounds per acre are usually employed. In some instances, lower rates may be utilized while higher rates may be necessary in other instances. In view of the foregoing and following disclosures, one skilled in the art can readily determine the optimum rate to be applied in any particular case.

So as to illustrate the general and selective phytotoxic properties of the active ingredients of the present invention, a group of controlled greenhouse experiments is described below.

In pre-emergence operations, seeds of selected species are planted in seedbeds and, while exposed, sprayed with a given volume of a solution containing a predetermined amount of the candidate active ingredient to provide the dosage rate desired. Such compositions are prepared by mixing the selected active ingredient and an emulsifier or dispersant with water. The seeds are then covered with a layer of soil and maintained under conditions conducive to growth. A portion of the planted seedbeds are left untreated to provide controls for comparative purposes. All seedbeds are watered as needed. About 14 days after seeding and treating, the effect of each test ingredient on the seeds is evaluated by a comparison with the control seedbeds.

In post-emergence operations, various species of plants are seeded in beds of good agricultural soil. After the plants have emerged and grown to a height of from about 2 to about 6 inches, certain of the plants are sprayed to run-off with a given volume of a composition prepared as set forth above. Other plants are left untreated to provide comparative controls. All plants are maintained as above for a period of about 14 days and then evaluated to determine the effect of the test ingredient.

In representative pre-emergence operations, the N'-(4-((6-chloro-2-pyrazinyl)oxy)phenyl)-N,N-dimethylurea compound was found to give substantial (70%) to complete (100%) control of the growth of German millett, barnyard grass, crabgrass, wild oat, pigweed, velvet leaf and annual morning glory seeds when contacted with the active ingredient at a rate of ten pounds per acre.

In representative post-emergence operations, the N'-(4-((6-chloro-2-pyrazinyl)oxy)phenyl)-N,N-dimethylurea compound was found to give from substantial to complete control of each of the above-named plant species when such plants are contacted with the active ingredient at a rate of ten pounds per acre. In selective post-emergence operations, the N'-(4-((6-chloro-2-pyrazinyl)oxy)phenyl)-N,N-dimethylurea compound was found to give substantial to complete control of German millett, barnyard grass, crabgrass, pigweed and annual morning glory plants at a rate of 2.5 pounds per acre without damage to rice and wheat plants.

The substituted halopyrazine, nitro(thio)phenol, carbamoyl halide, hydroxylamine, pyrrolidine and piperidine reactants employed in the preparation of the compounds of the present invention are either readily available or can be prepared by those skilled in the art according to procedures which are known or are analogous to those set forth in the prior art.

Although the invention is described with respect to specific embodiments and modifications, the details thereof are not to be construed as limitations except to the extent indicated in the following claims.

I claim:
1. N'-(4-((6-chloro-2-pyrazinyl)oxy)phenyl)-N,N-dimethylurea.

* * * * *

UNITED STATES PATENT AND TRADEMARK OFFICE
CERTIFICATE OF CORRECTION

PATENT NO. : 3,940,392
DATED : February 24, 1976
INVENTOR(S) : Howard Johnston

It is certified that error appears in the above–identified patent and that said Letters Patent are hereby corrected as shown below:

Column 6, line 8, "other" should read --Other--;

Column 7, line 28, "dichloro-2-pyrazinyl(thio)-3-cyano-" should read --dichloro-2-pyrazinyl)thio)-3-cyano- --;

Column 7, line 44, "pyrazinyl(oxy)phenyl-" should read --pyrazinyl)oxy)phenyl- --;

Column 8, line 40, "o)phenyl-1-piperidinecarboxamide;" should read --o)phenyl)-1-piperidinecarboxamide;--;

Column 8, line 43, "phenyl-N-" should read --phenyl)-N- --;

Column 10, line 60, "the plant to contacted" should read --the plant to be contacted--;

Column 10, line 64, "preemergence" should read --pre-emergence--.

Signed and Sealed this

Twenty-fourth Day of August 1976

[SEAL]

Attest:

RUTH C. MASON
*Attesting Officer*

C. MARSHALL DANN
*Commissioner of Patents and Trademarks*